(12) United States Patent
Chunduri et al.

(10) Patent No.: US 6,700,659 B1
(45) Date of Patent: Mar. 2, 2004

(54) SEMICONDUCTOR ANALYSIS ARRANGEMENT AND METHOD THEREFOR

(75) Inventors: Srikar V. Chunduri, Austin, TX (US); Glen P. Gilfeather, Del Valle, TX (US); Brennan V. Davis, Austin, TX (US); David H. Eppes, Austin, TX (US); Victoria Bruce, Austin, TX (US); Michael Bruce, Austin, TX (US); Rosalinda M. Ring, Austin, TX (US); Daniel Stone, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 173 days.

(21) Appl. No.: 09/838,671

(22) Filed: Apr. 19, 2001

Related U.S. Application Data

(60) Provisional application No. 60/198,365, filed on Apr. 19, 2000.

(51) Int. Cl.$^7$ .............................................. G01N 21/88
(52) U.S. Cl. .................................................. 356/237.5
(58) Field of Search ........................... 356/237.1–237.9; 438/141, 433; 359/908

(56) References Cited

U.S. PATENT DOCUMENTS

| | | | | |
|---|---|---|---|---|
| 5,759,424 A | * | 6/1998 | Imatake et al. | 216/60 |
| 6,395,563 B1 | * | 5/2002 | Eriguchi | 438/7 |

* cited by examiner

Primary Examiner—Tu T. Nguyen

(57) ABSTRACT

The operability of light-based semiconductor die analysis is enhanced using a method and arrangement that can detect light leakage between a light source and a die. In one example embodiment of the present invention, a light source is directed to a semiconductor analysis arrangement using, for example, a fiber optic cable. The analysis arrangement is adapted to use light from the light source for analyzing the die. A light detection arrangement detects a condition of light leakage from the system and generates a signal representing the condition of light leakage. The generated signal can then be used to control the semiconductor analysis arrangement, such as by deactivating the light source in response to a detected leak, or by allowing the light source to function in response to not detecting a leak.

33 Claims, 4 Drawing Sheets

SEMICONDUCTOR ANALYSIS ARRANGEMENT AND METHOD THEREFOR

RELATED PATENT DOCUMENTS

This Application claims priority for common subject matter to U.S. Provisional Patent Application Serial No. 60/198,365 (AMDA.475P1/TT3991), filed on Apr. 19, 2000 and entitled "Semiconductor Analysis Arrangement and Method Therefor," which is fully incorporated herein by reference. This application is further related to U.S. patent application Ser. No. 09/838,717 (AMDA.516PA/TT3991P1), entitled "Fiber Optic Semiconductor Analysis Arrangement and Method Therefor"; to U.S. patent application Ser. No. 09/838,667 (AMDAA.518PA/TT3991P3), entitled "Semiconductor Analysis Using Thermal Control", and to U.S. patent application Ser. No. 09/838,672 (AMDA.519PA/TT3991P4), now U.S. Pat. No. 6,635,839, entitled "Semiconductor Analysis Arrangement and Method Therefor," all of which are filed concurrently herewith.

FIELD OF THE INVENTION

The present invention relates generally to semiconductor device analysis and, more particularly, to devices and arrangements for enhancing the operability of semiconductor analysis.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of these technological advances has been an increase in the complexity of manufacturing of the devices, which has been accompanied by increased pressure to produce consistent and affordable products.

As the manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

One type of semiconductor analysis involves conveniently directing perturbation signals, such as laser light, to a semiconductor device under test (DUT). When performing such analysis, however, there are many issues to be managed. These issues include concerns such as laser leakage, calibration problems, and functional deficiencies. Further, there is a need for convenient approaches to presenting various types of perturbation signals to the DUT and to manage the DUT's response effectively and efficiently while maintaining an operable testing process.

SUMMARY OF THE INVENTION

The present invention is directed to an approach for improving semiconductor analysis. The present invention is exemplified in a number of implementations and applications, some of which are summarized below.

The present invention is directed to addressing needs discussed above and is further useful in connection with the example embodiments disclosed in the above-referenced patent documents. According to an example embodiment of the present invention a system is adapted to analyze a semiconductor die using detected light leakage from the system. A light source is coupled a semiconductor analysis arrangement that holds a semiconductor die and uses light from the light source for analyzing the die. The light source is coupled to the analysis arrangement using, for example, a fiber optic cable that directs light from the light source to the analysis arrangement. At least one light detection arrangement is adapted to detect whether light leaks from the fiber optic cable. The light detection arrangement may include, for example, a photodiode, a heat sensor and/or a die response detector. If a response is received from the light detection arrangement that is indicative of light leaking, the light source is deactivated. In this manner, light leakage can be detected and used to stop the light source to prevent further leakage during die analysis.

According to another example embodiment of the present invention, a system for analyzing a semiconductor die includes an arrangement adapted to detect light leakage. The system includes a test head adapted to hold the die and to provide an interface between the die and a chamber used to analyze the die. Once the test head is coupled with the chamber, one or more perturbation devices, such as laser, e-beam and ion beam devices, are used to analyze the die. Operation control data, such as chamber condition, die response, light leakage and other data, are provided to a processor programmed to evaluate the data relative to similar data obtained for a nondefective die undergoing the same types of tests and under similar conditions. The processor is further coupled to the test head and adapted to receive response data from the die, such as electrical data obtained from die outputs. The perturbation devices are also optionally coupled to the processor, and the processor can be adapted to control and receive feedback from the devices. A monitor is adapted to display information such as response data and control data. In one particular implementation, the monitor is used as part of an interface for controlling the system.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
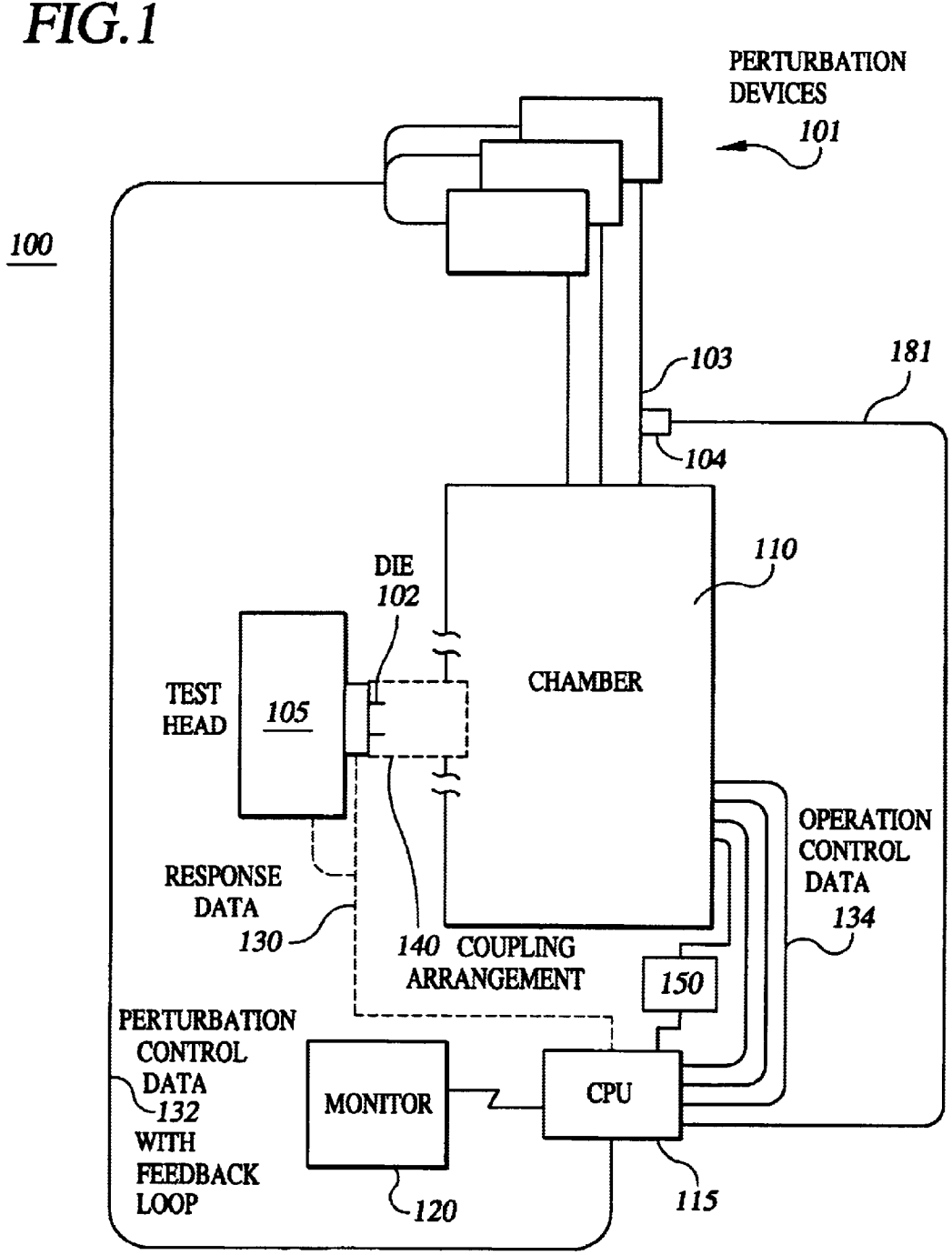
FIG. 1 is semiconductor analysis system, according to an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of analysis, and the invention has been found particularly suited for die analysis involving applications for multiple tools and detectors. While the present invention is not necessarily limited to such devices, various aspects of the invention may be appreciated through a discussion of various examples using this context.

According to an example embodiment of the present invention, a light detection device is used in connection with semiconductor die analysis that includes directing light to a semiconductor die. The detection device is adapted to detect a condition of light leakage between a light source and the die that could potentially approach a selected level. The condition of light leakage may, for example, be indicative of any light leakage, no light leakage or a measurable amount of light leakage. In one example implementation, a detector detects light that leaks, and in a second example implementation, a detector detects the amount of light passing between the light source and the die. In the first implementation, the amount of light escaping is detected, e.g., using a light detecting shroud surrounding a light-carrying channel and used to control the analysis. In a second example implementation, the amount of light passing to the die is detected and compared to a reference amount of light that is designed to be passed to the die. When the detected amount is less than the design amount, the difference in amount of light is an indication of a leak and is used as such to control the analysis.

In another example implementation, the light detection device includes a temperature sensor, such as a thermocouple, infrared temperature detector and/or commonly-used temperature sensor. The sensor is coupled between the light source and the die, such as to a fiber optic cable used to direct light to the die, and adapted to detect an increase in temperature caused by leaking light. For example, material surrounding a fiber optic cable typically heats in response to laser light incident upon it. The temperature sensor detects a corresponding increase in temperature and, in response, sends a signal representing the increase. When the temperature increase is related to a leakage amount approaching a selected level, the signal is used to deactivate the light source.

In another example implementation, the light detection device includes a circuit arrangement adapted to use a response from the die to detect an amount of light incident upon it. The response may include, for example, heat generated at the die, an electrical response, a passive response (e.g., photoemission and/or secondary electrons) or a light reflection from the die. The circuit arrangement may be coupled to the die via electrical pins or to detectors such as a microscope, an electron detector, and a photon detector. When a known response is expected in response to the light being directed to the die, a lack of the known response is used as an indication that a lesser amount of light than expected reaches the die. In this case, there is a possibility that light has leaked, and the light source is deactivated.

In a more particular example embodiment of the present invention, a system including the light detection device is calibrated based upon the reference amount of light that is detected passing through the fiber optic cable. The amount of light passing through the cable is detected and compared to the reference calibration obtained during calibration of the reference amount of light passing through the cable.

FIG. 1 shows a system 100 for analyzing a semiconductor die 102, according to an example embodiment of the present invention. The system includes a test head adapted to hold the die 102 and to dock with a chamber via a coupling arrangement. Once the test head is docked with the chamber, one or more perturbation devices 101, such as a FIB, laser, microwave, sonic, e-beam or ion beam device, is used to analyze the die. One of the perturbation devices includes a light-based device adapted to pass light through a fiber optic cable 103 having a light detector 104. The detector is adapted to detect light leakage from the fiber optic cable, and to send a signal that is an indication of leakage via communications link 181. Operation control data, such as chamber condition, die response, the light leakage signal and other data is provided to a controller 115. The controller is further adapted to receive response data from the die, such as electrical data obtained from die outputs. The perturbation devices 101 are also optionally coupled to the controller 115, and the controller can be adapted to control and receive feedback from the devices 101. A monitor 120 is coupled to the controller 115 and adapted to display information such as response data, control data and leakage data from the detection device 104. In one particular implementation, the monitor is used as part of an interface for controlling the system 100. In another particular implementation, the controller is programmed to stop the light-based perturbation device in response to the leakage data indicating a selected amount of leakage, such as a light leak that would not adversely affect analysis of the die, or meet other operational leakage standards. Stopping the light-based perturbation device may, for example, include cutting power to the device.

In another example embodiment of the present invention, the system 100 includes a debug relay 150 communicatively coupled to the semiconductor analysis arrangement and adapted to detect a failure condition of the analysis arrangement. The detected failure condition is relayed to the CPU 115 via a signal generated in response to the failure condition. The CPU sends a signal to the photodiode, which is adapted to detect light passing through the selected portion of the fiber optic cable in response to the debug relay.

Figure 2:
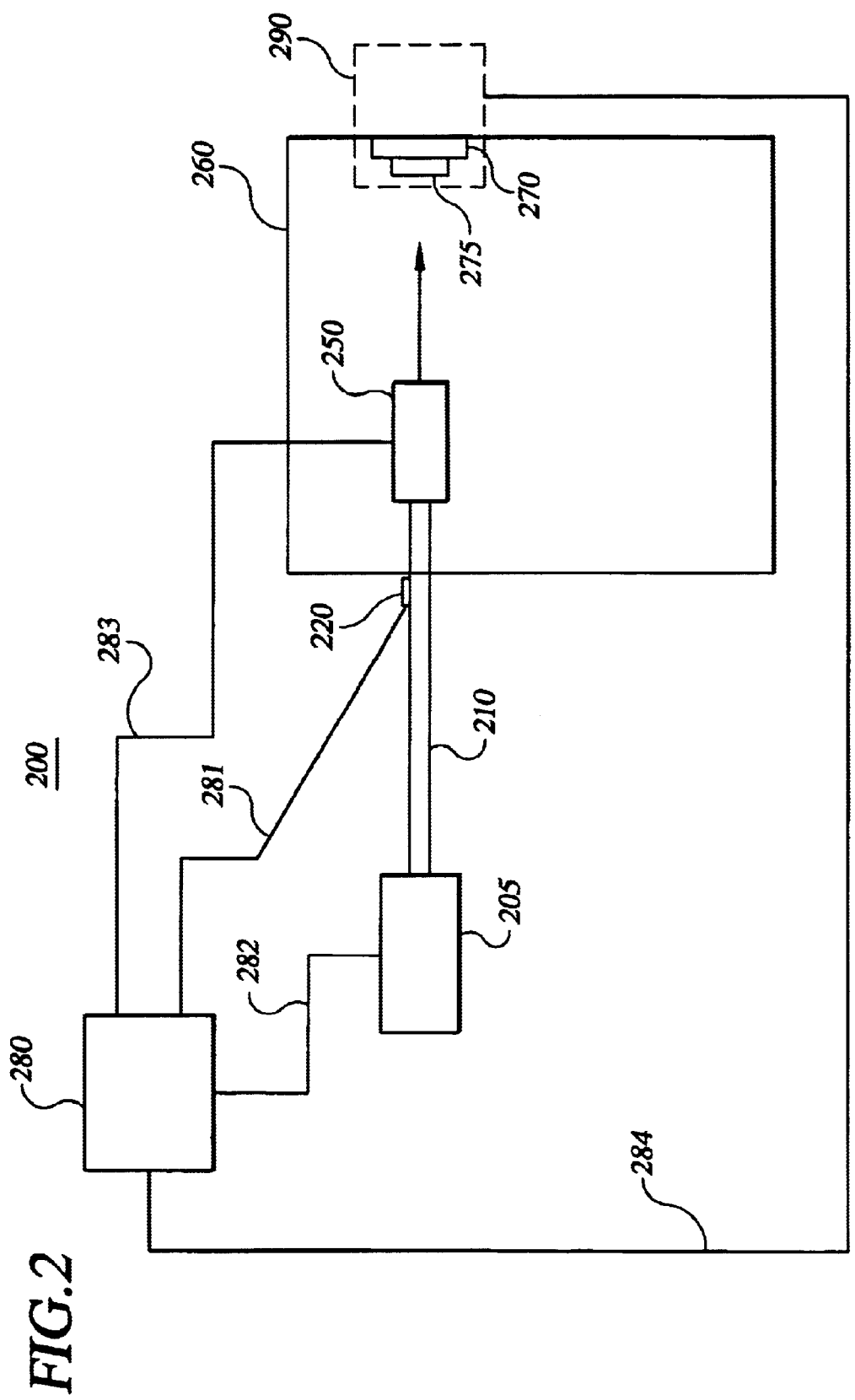
FIG. 2 shows a system adapted to analyze a semiconductor die, according to another example embodiment of the present invention.

In another more particular example embodiment of the present invention, FIG. 2 shows a fiber optic system 200 adapted to analyze a semiconductor die 275. The die is placed on a die holder 270 in a test chamber 260. In one implementation, the holder 270 is part of a docking arrangement 290. For further examples of docking arrangements suitable for use in connection with this example embodiment, reference may be made to U.S. patent application Ser. No. 09/838,672 (AMDA.519PA/TT3991P4), now U.S. Pat. No. 6,635,839, filed concurrently herewith and fully incorporated herein by reference. A light source 205, such as a laser source, generates light and the light is directed to the die 275 via a fiber optic cable 210 and through a die analysis arrangement 250. The fiber optic cable may include, for example, a primary fiber optic waveguide surrounded by a protective waveguide. A photodiode 220 is coupled to the fiber optic cable, is communicatively coupled to a controller 280 via communications link 281 and is adapted to detect light leakage from the cable. In response to an amount of light that might leak from the cable, the photodiode generates a signal that is sent to the controller 280. The contoller receives the signal and uses it for controlling the analysis of the semiconductor die 275.

The controller is adapted to receive a response from the die 275. For instance, the response may be detected in the chamber 260 at the die analysis arrangement 250 and sent to the controller via a communications link 283. In another instance, the response is detected from an output of the die 275 and is sent to the controller via communications link 284.

In one implementation, the signal from the photodiode is used to calibrate the system. The calibration can be used for determining a reference amount of light passing through the cable. For example, the light source can be powered prior to performing analysis. The photodiode is used to detect the amount of light passing through the fiber optic cable. Once the amount of light is known, subsequent measurements can be made to ensure that the amount of light hasn't changed, or to determine the amount of change in the light delivered. This is useful, for example, to ensure that a selected amount of light reaches the die 275 and/or to ensure that any leakage of the light is within an acceptable level for the particular application.

In another implementation, the signal from the photodiode is used to enhance die analysis as follows: when the amount of light that escapes from the fiber optic cable reaches a threshold level corresponding to a selected amount of light that approaches a level designated as prohibited by OSHA, a warning is generated at the controller. The warning may include, for example, a warning light that is adapted to provide an operator with an indication that the amount of light leaking is approaching the prohibited level. When the warning signal is generated, the controller is adapted to take measures to enhance the analysis. This may include, for example, sending a signal via communications link 282 to shut down the light source 205.

In another example implementation of the present invention, a photodiode is located inside the chamber 260. This is useful for various applications including those that benefit from the ability to detect light leakage within the chamber without necessarily accessing the inside of the chamber. For instance, one application involves drawing a vacuum on the chamber during die analysis. If the chamber needs to be opened, the vacuum is lost. By previously placing the photodiode inside the chamber, calibration, monitoring and other aspects of the light delivery through the fiber optic cable can be realized without necessarily opening the chamber and breaking the vacuum. This makes possible the analysis of a die under vacuum while realizing the benefits of monitoring the light delivery concurrently with the analysis.

In addition to laser beam analysis, the present invention can be adapted to provide other types of analysis, such as that employing an ion beam or an electron beam. The beams can be used individually or in conjunction with each other for die analysis. In this manner, various types of analysis, such as those employing laser scanning for defect detection, can be performed in a single test arrangement. For more information regarding example types of analysis that can be performed in connection with the present invention, reference may be made to the following: U.S. Pat. No. 5,430,305, entitled "Light-Induced Voltage Alteration for Integrated Circuit Analysis, filed on Apr. 8, 1994; U.S. Pat. No. 5,523,694, entitled "Integrated Circuit Failure Analysis by Low-Energy Charge-Induced Voltage Alteration," filed on Jun. 4, 1996; U.S. Pat. No. 5,844,416, entitled "Ion-Beam Apparatus and Method for Analyzing and Controlling Integrated Circuits," filed on Nov. 2, 1995; U.S. patent application Ser. No. 09/259,542, now U.S. Pat. No. 6,177,989, entitled "Laser Induced Current for Semiconductor Defect Detection," filed on Mar. 1, 1999; U.S. patent application Ser. No. 09/187,314 (AMDA.263PA), now U.S. Pat. No. 6,146,014, entitled "Method for Laser Scanning Flip-Chip Integrated Circuits," filed on Nov. 4, 1998; and U.S. patent application Ser. No. 09/385,775, now U.S. Pat. No. 6,541, 987, entitled "Laser-Excited Detection of Defective Semiconductor Device," filed on Aug. 30, 1999; which are fully incorporated herein by reference.

Figure 3:
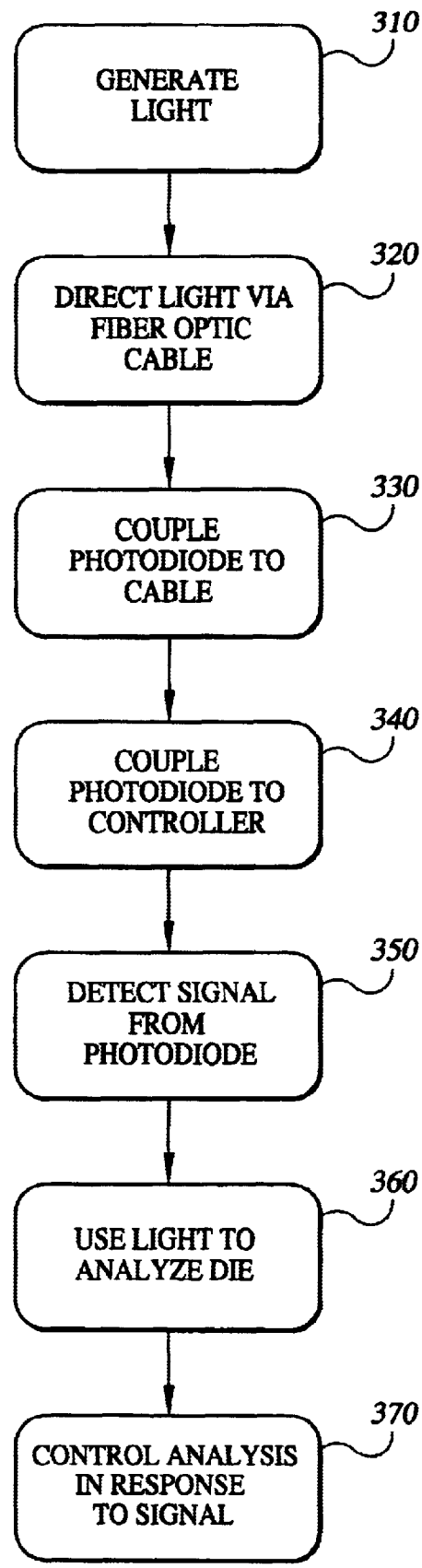
FIG. 3 is a flow diagram of a method for analyzing a semiconductor die, according to another example embodiment of the present invention.

FIG. 3 is a flow diagram of a method for analyzing a semiconductor device, according to another example embodiment of the present invention. Light is generated at block 310, and the generated light is directed via a fiber optic cable at block 320. A photodiode is coupled to the fiber optic cable at block 330 and is adapted to detect light passing through the cable. The photodiode is coupled to a controller at block 340, a signal representing the detected light is detected from the photodiode at block 350, and the signal is used by the controller for analyzing the die at block 360. By detecting variations in the strength of the signal, a change in the amount of light passing through the cable can be detected. At block 370, the analysis of the die is controlled in response to the signal in a manner that includes controlling the light generation in response to a change in the amount of light passing through the cable being indicative of light escaping from the cable.

Figure 4:
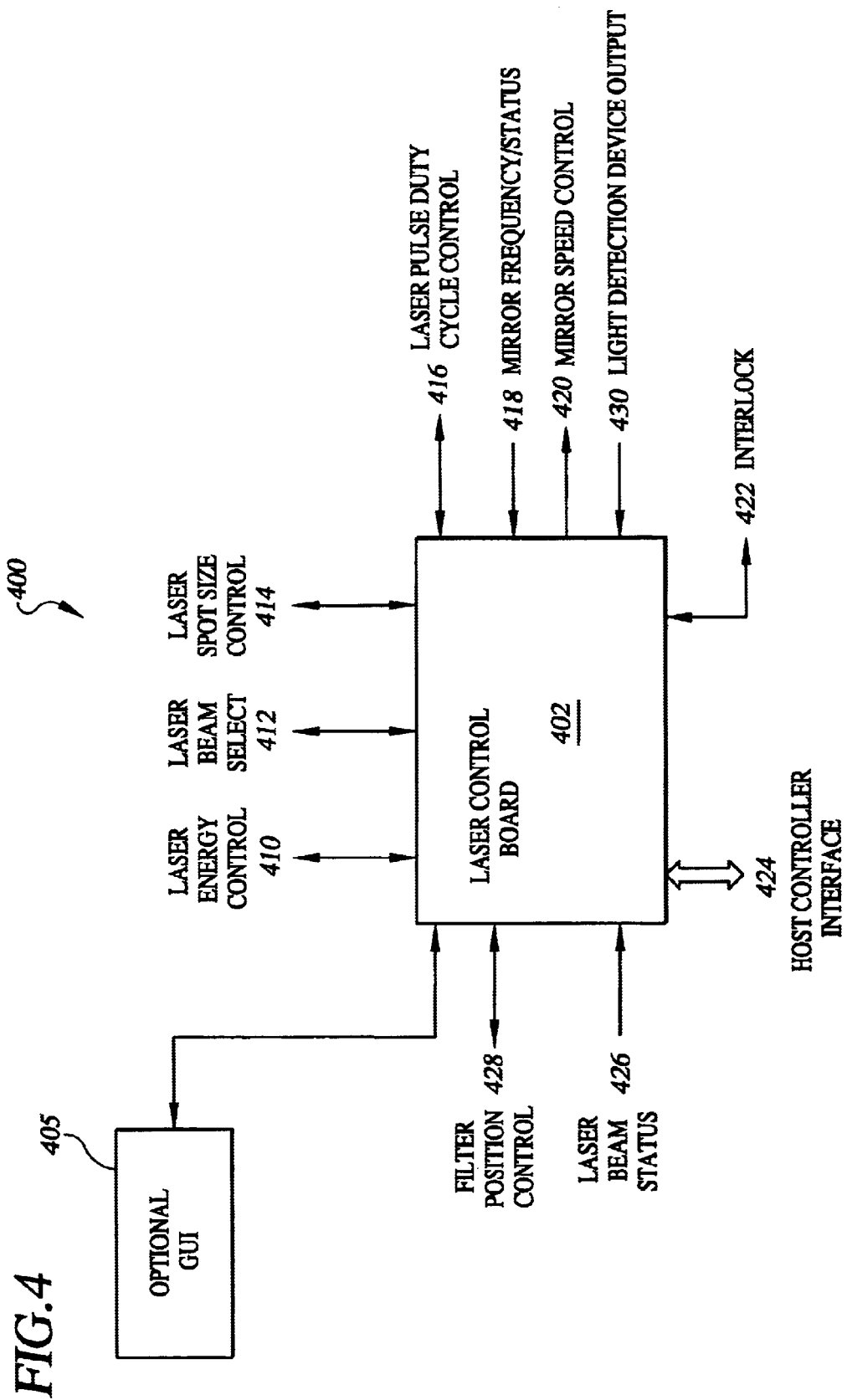
FIG. 4 is a system for controlling a semiconductor analysis arrangement, according to another example embodiment of the present invention.

FIG. 4 is a laser controller 400, according to another example embodiment of the present invention. The controller may be used, for example, in connection with the analysis systems and methods described herein, such as that shown in FIGS. 1–2. The controller 400 includes a board 402 having a variety of input and output ports. The ports include laser energy control 410, laser beam selection 412, laser spot size control 414, laser pulse duty cycle control 416, mirror frequency and status input 418, mirror speed control 420, interlock 422, host controller interface 424, laser beam status 426 and filter position control 428. Each of these ports is used to communicate signals for effecting the control and/or function related to its identification, such as for positioning the laser and related equipment, for controlling the power and configuration of the laser and for ensuring interlocks, such as a chamber door being closed, are in place. The interlock port 422 may, for example, be coupled to a light detection arrangement, such as one including the light detector 104 of FIG. 1 and/or the photodiode 220 in FIG. 2. When the interlock 422 receives a signal that is indicative of an interlock failing (e.g., a detected light leak), the laser energy control port 410 is used to turn the laser off, and a laser beam status 426 is used to verify that the beam is indeed off.

In a more particular example implementation, the controller 400 includes a graphical user interface (GUI) 405. The GUI is adapted to provide operator control of a laser analysis system. The GUI can be adapted to control various items, such as gas, temperature, cooling, beam focusing, signal latching, test configuration, monitor selections including contrast, brightness and color selection, scanning features, dwell time, scanning rate control, spot control, internal tool selection (e.g. with various analysis techniques, such as a dual-beam arrangement, photon beam analysis, TIVA, LIVA, OBIC, OBIRCH and CTP), and imaging controls such as overlays, labeling images and image processing.

In another implementation, the GUI is adapted to control the operation of the laser energy control output. In one instance, the GUI is adapted to receive an input from a user that corresponds to a threshold level of light detected using, for example, a light detection device output 430. The light detection output may include an output from a device such as the photodiode 220 of FIG. 2 and/or light detection device 104 of FIG. 1. In one implementation wherein light passing to a test arrangement is detected, the light detection output 430 is compared to the threshold input from the GUI at the laser control board. When the output is less than the threshold, there is a leak in the system before the detector (e.g., in the fiber optic cable 210 of FIG. 2). In this instance, the laser energy control 410 is stopped in response to the output dropping below the threshold.

In another instance, the controller includes a comparison arrangement coupled to the interlock 422. The comparison arrangement is coupled and adapted to receive a signal representative of light leaking from an analysis system, such as those described herein. The signal is compared to a threshold, and when the threshold is exceeded, a signal is sent to the laser board via the interlock 422. In response, the laser energy control port is used to stop the laser.

While the present invention has been described with reference to several particular example embodiments, those skilled in the art will recognize that changes may be made thereto without departing from the spirit and scope of the present invention, which is set forth in the following claims.

What is claimed is:

1. A system adapted to analyze a semiconductor die, the system comprising:
   a light source adapted to generate light;
   a semiconductor analysis arrangement adapted to hold the semiconductor die and to use light from the light source for analyzing the die;
   a fiber optic cable coupled between the light source and the analysis arrangement and adapted to direct the generated light from the light source to the die for analyzing the die at the analysis arrangement; and
   a light detection arrangement adapted to detect a condition of light leakage from the system and to generate a signal representing the condition of light leakage to be used to control the semiconductor analysis arrangement.

2. The system of claim 1, further comprising a controller adapted to control the semiconductor analysis arrangement.

3. The system of claim 2, wherein the controller is communicatively coupled to the light detection arrangement and adapted to receive a signal representing a condition of the fiber optic cable from the light detection arrangement and to control the analysis of the semiconductor die in response to the received signal.

4. The system of claim 3, wherein the signal varies in relation to light that escapes from the fiber optic cable.

5. The system of claim 2, wherein the controller is communicatively coupled to the light detection arrangement and adapted to shut down the light source in response to receiving a signal from the light detection arrangement that is indicative of a leak approaching a prohibited level in the fiber optic cable.

6. The system of claim 5, wherein the controller includes a GUI adapted to receive a user input and to use the input as a threshold value and to compare the threshold value to the signal from the light detection arrangement, wherein the signal being below the threshold value is indicative of the leak approaching the prohibited level.

7. The system of claim 2, wherein the controller includes a computer.

8. The system of claim 1, wherein the fiber optic cable includes a primary fiber optic waveguide surrounded by a protective fiber optic waveguide.

9. The system of claim 1, wherein the light detection arrangement includes a photodiode located adjacent a portion of the fiber optic cable nearest the analysis arrangement.

10. The system of claim 1, wherein the fiber optic cable extends into the analysis arrangement and is adapted to direct light to a semiconductor die held in the analysis arrangement.

11. The system of claim 1, further comprising a debug relay communicatively coupled to the semiconductor analysis arrangement and adapted to detect a failure condition or the analysis arrangement and to generate a signal in response to the failure condition, and wherein the light detection arrangement is adapted to detect a condition of light leakage from the system in response to the debug relay.

12. The system of claim 1, wherein the light source includes a laser source.

13. The system of claim 1, wherein the semiconductor analysis arrangement includes a test chamber having a fixture adapted to hold the semiconductor die.

14. The system of claim 13, wherein the analysis arrangement is adapted to evacuate the test chamber.

15. The system of claim 14, wherein the light detection arrangement includes at least one photodiode located within the test chamber and adapted to detect light that passes through a selected portion of the fiber optic cable while the chamber is under a vacuum.

16. The system of claim 13, wherein the fixture is part of a test head arrangement that is separate from the test chamber, and wherein the test head arrangement and the test chamber are adapted to dock together to form an enclosed chamber.

17. A system adapted to analyze a semiconductor die, the system comprising:
   a light source adapted to generate light;
   a semiconductor analysis arrangement adapted to hold the semiconductor die and to use light from the light source for analyzing the die;
   a fiber optic cable coupled between the light source and the analysis arrangement and adapted to direct the generated light from the source to the die for analyzing the die at the analysis arrangement; and
   a light detection arrangement adapted to detect a condition of light leakage from the system and to generate a signal representing the condition of light leakage to be used to control the semiconductor analysis arrangement including at least one photodiode coupled to the fiber optic cable and adapted to detect light leaking from the fiber optic cable and to generate a signal representing the detected light to be used to control the semiconductor analysis arrangement.

18. A system adapted to analyze a semiconductor die, the system comprising:
   a light source adapted to generate light;
   a semiconductor analysis arrangement adapted to hold the semiconductor die and to use light from the light source for analyzing the die;
   a fiber optic cable coupled between the light source and the analysis arrangement and adapted to direct the generated light from the light source to the die for analyzing the die at the analysis arrangement; and
   a light detection arrangement adapted to detect a condition of light leakage from the system and to generate a signal representing the condition or light leakage to be used to control the semiconductor analysis arrangement including a temperature sensor adapted to detect a change in temperature caused by light leaking from the fiber optic cable and to generate a signal representing the temperature change to be used to control the semiconductor analysis arrangement.

19. A system adapted to analyze a semiconductor die, the system comprising:

a limit source adapted to generate light;

a semiconductor analysis arrangement adapted to hold the semiconductor die and to use light from the light source for analyzing the die;

a fiber optic cable coupled between the light source and the analysis arrangement and adapted to direct the generated light from the light source to the die for analyzing the die at the analysis arrangement; and a light detection arrangement adapted to detect a condition of light leakage from the system and to generate a system representing the condition of light leakage to be used to control the semiconductor analysis arrangement including a circuit arrangement adapted to use a response from the die to detect an amount of light incident upon it and to generate a signal representing the die response to be used to control the semiconductor analysis arrangement.

20. The system of claim 19, wherein the circuit arrangement is adapted to detect a response that includes at least one of: heat generated at the die, an electrical response from the die, a passive response from the die and a light reflection from the die.

21. A system adapted to analyze a semiconductor die, the system comprising:

a light source adapted to generate light;

a semiconductor analysis arrangement adapted to hold the semiconductor die and to use light from the light source for analyzing the die;

a fiber optic cable coupled between the light source and the analysis arrangement and adapted to direct the generated light from the light source to the die for analyzing the die at the analysis arrangement; and a light detection arrangement adapted to detect a condition of light leakage from the system and to generate a signal representing the condition of light leakage to be used to control the semiconductor analysis arrangement including at least one photodiode coupled to the fiber optic cable and adapted to detect light passing through a selected portion or the fiber optic cable, the detected light being indicative of a condition of light leakage from the cable, and to generate a signal representing the detected light to be used to control the semiconductor analysis arrangement.

22. A system adapted to analyze a semiconductor die, the system comprising:

a light source adapted to generate light;

a semiconductor analysis arrangement adapted to hold the semiconductor die and to use light from the light source for analyzing the die;

a fiber optic cable coupled between the light source and the analysis arrangement and adapted to direct the generated light from the light source to the die for analyzing the die at the analysis arrangement;

a light detection arrangement adapted to detect a condition of light leakage from the system and to generate a signal representing the condition of light leakage to be used to control the semiconductor analysis arrangement; and a controller adapted to control the semiconductor analysis arrangement and the controller is communicatively coupled to the light detection arrangement and adapted to receive a signal representing a condition of the fiber optic cable from the light detection arrangement and to control the analysis of the semiconductor die in response to the received signal and the signal varies in relation to light that escapes from the fiber optic cable and the controller is further adapted to calibrate the system based upon a reference amount of light that passes through the fiber optic cable, and wherein further analysis of the amount of light passing through the cable is performed by comparing a signal from the light detection arrangement with a reference signal obtained during calibration of the reference amount of light passing through the cable.

23. A system adapted to analyze a semiconductor die, the system comprising:

means for generating light;

means for directing the generated light to the die at a die analysis arrangement;

means for holding the semiconductor die and using the generated light to analyze the die; and means for detecting a condition of light leakage from the system and generating a signal representing the condition of light leakage to be used to control the semiconductor analysis.

24. A method for analyzing a semiconductor die, the method comprising:

generating light;

directing the generated light to the die at a die analysis arrangement;

holding the semiconductor die and using the generated light to analyze the die; and detecting a condition of light leakage from the system and generating a signal representing the condition of light leakage to be used to control the semiconductor analysis.

25. The method of claim 24, wherein generating light includes generating laser light.

26. The method of claim 24, further comprising comparing the generated signal to a threshold signal, the threshold signal representing a leakage amount that corresponds to a selected threshold.

27. The method of claim 26, wherein detecting a condition of light leakage includes detecting that the light leakage reaches a threshold corresponding to a level near a prohibited threshold level, further comprising generating a warning.

28. The method of claim 26, wherein detecting a condition of light leakage includes detecting that the light leakage reaches a threshold corresponding to a prohibited threshold level, further comprising stopping the light generation in response to reaching the prohibited threshold level.

29. The method of claim 24, further comprising detecting a signal from a debug relay adapted to provide a signal indicative of a failure condition, and detecting a condition of light leakage includes detecting the condition in response to the debug relay.

30. The method of claim 24, wherein directing the generated light to the die includes directing the generated light via a fiber optic cable.

31. The method of claim 30, further comprising:

coupling at least one photodiode to the fiber optic cable, the photodiode being adapted to detect light passing through the fiber optic cable;

communicatively coupling the photodiode to a controller adapted to control the die analysis arrangement; and detecting a signal from the photodiode that represents a condition of light leakage from the fiber optic cable and controlling the analysis arrangement in response thereto.

32. A method for analyzing a semiconductor die, the method comprising:

generating light;

directing the generated light to the die at a die analysis arrangement;

holding the semiconductor die and using the generated light to analyze the die; and detecting a condition of light leakage from the system including includes detecting a leak in a fiber optic cable and generating a signal representing the condition of light leakage to be used to control the semiconductor analysis.

33. A system adapted to analyze a semiconductor die, the system comprising:

a light source adapted to generate light;

a semiconductor analysis arrangement adapted to hold the semiconductor die and to use light from the light source for analyzing the die;

a fiber optic cable coupled between the light source and the analysis arrangement and adapted to direct the generated light from the light source to the die for analyzing the die at the analysis arrangement; and a light detection arrangement including a photodiode and adapted to detect a condition of light leakage from the system and to generate a signal representing the condition of light leakage to be used to control the semiconductor analysis arrangement.

* * * * *

UNITED STATES PATENT AND TRADEMARK OFFICE
CERTIFICATE OF CORRECTION

PATENT NO. : 6,700,659 B1
DATED : March 2, 2004
INVENTOR(S) : Chunduri et al.

It is certified that error appears in the above-identified patent and that said Letters Patent is hereby corrected as shown below:

Column 5,
Line 1, "contoller" should read -- controller --.

Column 11,
Line 16, delete "includes".

Signed and Sealed this

Sixth Day of July, 2004

JON W. DUDAS
*Acting Director of the United States Patent and Trademark Office*